(12) United States Patent
Mohr et al.

(10) Patent No.: US 7,214,651 B2
(45) Date of Patent: May 8, 2007

(54) DISINFECTANT HAVING IMPROVED ACTIVITY AGAINST MYCOBACTERIA

(75) Inventors: Michael Mohr, Kaltenkirchen (DE); Peter Goroncy-Bermes, Hamburg (DE)

(73) Assignee: Air Liquide Sante (International), Paris (FR)

( * ) Notice: Subject to any disclaimer, the term of this patent is extended or adjusted under 35 U.S.C. 154(b) by 6 days.

(21) Appl. No.: 11/266,642

(22) Filed: Nov. 3, 2005

(65) Prior Publication Data

US 2006/0094638 A1    May 4, 2006

(30) Foreign Application Priority Data

Nov. 3, 2004    (DE)    ........................ 10 2004 053 141

(51) Int. Cl.
*C11D 3/48*    (2006.01)
*C11D 1/72*    (2006.01)

(52) U.S. Cl. ................. 510/161; 510/253; 510/382; 510/384; 510/401; 510/421; 510/432; 510/504

(58) Field of Classification Search ................. 510/253, 510/161, 382, 384, 401, 421, 432, 504
See application file for complete search history.

(56) References Cited

U.S. PATENT DOCUMENTS 5,185,145 A * 2/1993 Eggensperger et al. .. 424/78.08

5,393,789 A    2/1995 Eggensperger et al.

FOREIGN PATENT DOCUMENTS

| | | |
|---|---|---|
| DE | 35 14 689 | 11/1986 |
| DE | 40 05 784 | 8/1991 |
| DE | 42 01 038 | 7/1993 |
| DE | 43 21 566 | 1/1995 |
| DE | 199 09 303 | 9/2000 |
| DE | 19909303 * | 9/2000 |
| DE | 100 28 998 | 8/2001 |
| DE | 299 24 225 | 8/2002 |
| EP | 0 551 975 | 7/1993 |
| EP | 1 126 012 | 8/2001 |
| EP | 1 138 203 | 10/2001 |
| FR | 2 710 919 | 4/1995 |

OTHER PUBLICATIONS

European Search Report for EP 05 10 9398.

* cited by examiner

*Primary Examiner*—Charles Boyer
(74) *Attorney, Agent, or Firm*—Brandon Clark

(57) ABSTRACT

Methods and compositions for a concentrated alkaline disinfectant. The disinfectant includes a quaternary ammonium salt, a guanidine derivative, an alcohol ethoxylate with between 5 and 7 EO units, alkylamine, an acid, and aromatic alcohol.

14 Claims, No Drawings

DISINFECTANT HAVING IMPROVED ACTIVITY AGAINST MYCOBACTERIA

CROSS-REFERENCE TO RELATED APPLICATIONS

This application claims the benefit of priority under 35 U.S.C. § 119 (a) and (b) to German Application No. 10 2004 053 141.2, filed Nov. 3, 2004, the entire contents of which are incorporated herein by reference.

BACKGROUND

The present invention relates to an alkaline disinfectant in the form of a concentrate and an aqueous ready-to-use solution. The invention further relates to the use of the composition as instrument disinfectant and for controlling mycobacteria. Furthermore, the invention relates to the use of alcohol ethoxylates having 5–7 EO units for improving the mycobactericidal activity of a disinfectant which contains quaternary ammonium salt.

Disinfectants for use against mycobacteria are known. Thus EP 1 138 203 A2 describes an active compound combination of aldehyde and at least one nonionic surfactant selected from the group of the $C_6$ to $C_{10}$-alcohol ethoxylates having 2 to 8 EO units. The cleaning performance when this active compound combination is used, however, is unsatisfactory.

Further disinfectants are described in the laid-open publications DE 199 09 303 A1, DE 42 01 038 AL, DE 100 28 998 A1 and DE 40 05 784 A1. Disinfectants are also known which contain no cationic compound and nevertheless are active against mycobacteria, fungi and viruses, see DE 42 01 038 A1.

Disinfectants having activity against mycobacteria, in particular disinfectants for disinfecting instruments and surfaces, are
- to be able to be formulated, not only as concentrate, but also as dilute ready-to-use solution (for example, as dilute ready-to-use solution in hard water) to give clear solutions so that in use, in particular in instrument disinfection, they leave no residues behind,
- to be active even at very low usage concentration of the active compounds,
- to be able to be formulated from inexpensive and commercially conventional components,
- to be material-compatible,
- to have little to no odor nuisance, and
- to have good cleaning performance.

SUMMARY

It was therefore an object of the invention to provide a disinfectant which conforms to these requirements, which can be formulated as concentrate, and also meets the above-mentioned requirements as dilute (aqueous) ready-to-use solution.

It has now surprisingly been found that this object is achieved by an alkaline disinfectant in the form of a concentrate which includes
  a) about 0.5 to about 10% by weight of quaternary ammonium salt,
  b) about 1 to about 50% by weight of guanidine derivative,
  c) about 1 to about 30% by weight of $C_{10}$- to $C_{18}$-alcohol ethoxylate having 5 to 7 EO units,
  d) about 1 to about 15% by weight of alkylamine,
  e) about 0.05 to about 3% by weight of maleic acid and/or citric acid, and
  f) about 5 to about 60% by weight of aromatic alcohol.

The invention includes both methods and compositions to achieve the desired results, as described, but is not limited to the various embodiments disclosed.

DESCRIPTION OF PREFERRED EMBODIMENTS

The invention includes methods and compositions for alkaline disinfectants, as described above.

The inventive concentrate is preferably a clear solution and may be diluted with water, also with hard water, to give a clear dilute ready-to-use solution. Therefore, the invention is also achieved by the dilute ready-to-use solution. The inventive concentrate has a pH of preferably about 8, more preferably about 8.5 to about 10, in particular about 9 to about 9.5, for instance, about 9.3. The inventive dilute ready-to-use solution has a pH of preferably >7.5, more preferably >8, in particular about 8.3 to about 9.0, for example, about 8.5.

Preferred quaternary ammonium salts are described by the formulae $[R^1R^2R^3R^4N]^+[X]^-$ and $[N-R^5\text{-pyridinium}]^+[X]^-$, where $R^1$ to $R^5$ can be identical or different and are selected from $C_1$ to $C_{30}$-alkyl, $C_1$ to $C_{30}$-alkenyl and $C_1$ to $C_{30}$-aryl and mixed groups, which can have one or more atoms selected from O, S, N and P, where one or more of $R^1$ to $R^4$ can also be H, with the proviso that at least one of the groups $R^1$ to $R^4$ is different from H. X is an anion (of an organic or inorganic acid). Not only anion but also cation of the quaternary ammonium salt can be polyvalent ions which results in a stoichiometry $[A^{(n+)}]_m[K^{(m+)}]_n$.

Quaternary ammonium salts preferably used according to the invention are $[R^1N(CH_3)_3]^+[X]^-$, $[R^1NH_3]^+[X]^-$, $[R^1(\text{aryl}CH_2)NH_2]^+[X]^-$, $[R^1(\text{aryl}CH_2)N(CH_3)_2]^+[X]^-$, $[R^1R^2N(CH_3)_2]^+[X]^-$ and $[N-R^5\text{-pyridinium}]^+[X]^-$, where $R^1$, $R^2$ and $R^5$ independently of one another are selected from $C_1$- to $C_{30}$-alkyl, $C_6$- to $C_{12}$-aryl and $-(CH_2\text{-}CHR^6O)_n-R^7$, where n is a number from 1 to 20 and $R^6$ and $R^7$, which can be identical or different, are H and/or $C_1$- to $C_4$-alkyl, and aryl is an aryl group which is unsubstituted or substituted.

Exemplary cations of the quaternary ammonium salts used inventively are $C_8$- to $C_{18}$-alkylbenzylammonium, benzalkonium, didecyl- and dioctyldimethylammonium, didecylmethylpoly(oxyethyl)ammonium, cetylpyridinium, cetyltrimethylammonium and benzyl fatty alkyl-bis(hydroxy-ethyl)ammonium and also mixtures of the same. Exemplary anions and classes of anions of the quaternary ammonium salts used inventively are hydroxide, sulphate, hydrogen sulphate, halide (fluoride, chloride, bromide, iodide), nitrite, nitrate, carbonate, hydrogen carbonate, phosphate, and carboxylate salt such as benzoate, lactate, acetate, propionate and citrate. A particularly preferred anion is chloride. A quaternary ammonium salt preferred in all embodiments of the invention is benzalkonium chloride.

Preferably, the amount of the quaternary ammonium salt (or of the two, three, four, etc. quaternary ammonium salts) is about 1 to about 5% by weight, more preferably about 2 to about 3% by weight, for example, about 2.5% by weight. In aqueous solution, quaternary ammonium salts are known to be present in dissociated form, and their amount is therefore reported as quaternary ammonium chloride. In a particularly preferred embodiment, benzalkonium chloride is used in the concentrate at a concentration of about 2.5% by weight.

The inventive disinfectant comprises at least one guanidine derivative. A particularly preferred guanidine derivative is cocopropylenediamine guanidinium acetate. In addition polyhexamethylenebiguanidinium hydrochloride and dodecylguanidinium acetate are suitable.

Preferably, the amount of the guanidine derivative (or of the two, three, four, etc. guanidine derivatives) is about 5 to about 30% by weight, more preferably about 10 to about 20% by weight, for example, about 14% by weight. In a preferred embodiment, cocopropylenediamine guanidinium acetate is used in an amount of about 14% by weight in the concentrate.

The inventively used alcohol ethoxylates correspond to the formula $R(OCH_2CH_2)_nOH$, where the group R of the underlying alcohol is a linear or branched $C_{10}$- to $C_{18}$-alkyl group, preferably $C_{10}$ to $C_{15}$, such as $C_{10}$ to $C_{13}$, for example, a $C_{10}$-$C_{11}$- or $C_{13}$-isoalkyl group derived from an oxoalcohol, and n=5 to 7, such as 5, 6 or 7.

The invention is based, inter alia, on the fact that it has been found that, by using a $C_{10}$- to $C_{16}$-alcohol alkoxylate having 5 to 7 mol of ethylene oxide, the activity of a defined disinfectant against mycobacteria, for example, *Mycobacterium terrae*, can be improved, compared with the activity of an otherwise essentially unchanged disinfectant which contains a nonionic disinfectant having more than 7 ethylene oxide units. Although the inventively used alcohol ethoxylate having a relatively short EO chain (5 to 7 EO) exhibits a relatively lower cleaning power, this is compensated for by a suitable selection of the other components used according to the invention.

Alcohol ethoxylates having fewer than 5 ethylene oxide units are preferably not present in the inventive composition (concentrate, ready-to-use solution), because these surfactants are relatively sparingly soluble in the dilute ready-to-use solution and this solubility is not caused by the other constituents of the inventive composition (for example, the quaternary ammonium salts).

Furthermore, when a nonionic surfactant having 5 to 7 ethylene oxide units is used, the surface tension of the ready-to-use solutions is lowered, and, even when a relatively small amount is used, the activity against mycobacteria is increased, compared with a nonionic surfactant having for example, 10 to 13 ethylene oxide units.

Furthermore, other nonionic surfactants can also be present, for example, alcohol ethoxylates having more than 7 EO units and/or a $C_4$- to $C_9$-alcohol group. In the examples it is demonstrated that with complete replacement of an alcohol ethoxylate having 12 EO units by the $C_{10}$- to $C_{18}$-alcohol ethoxylate having 5 EO units, the total amount required of nonionic surfactant can be lowered. In an alternative embodiment, according to the invention only a part of the alcohol ethoxylate is replaced by $C_{10}$- to $C_{18}$-alcohol ethoxylate having 5 to 7 EO units. Then, no impairment of the cleaning performance occurs, as can occur with complete replacement of the non-inventive alcohol ethoxylate by $C_{10}$- to $C_{18}$-alcohol ethoxylate having 5 to 7 EO units in an essentially unchanged formulation. In this alternative embodiment also, improvement of the activity against mycobacteria occurs. In this alternative embodiment, the proportion of $C_{10}$- to $C_{18}$-alcohol ethoxylate having 5 to 7 ethylene oxide units, based on the total amount of alcohol ethoxylate, is about 10 to about 90% by weight, such as about 30 to about 70% by weight, for example, about 50% by weight.

Preferably, the amount of the $C_{10}$- to $C_{18}$-alcohol ethoxylate having 5 to 7 EO units (or of the corresponding two, three, four, etc. alcohol ethoxylates) is about 2 to about 20% by weight, more preferably about 5 to about 15% by weight, in particular about 8 to about 12% by weight, for example, about 10% by weight, based on the concentrate. In a particularly preferred embodiment, triisodecanol-5EO is used in the concentrate in an amount of about 10% by weight.

According to the invention, the alkylamine is preferably selected from the group of fatty amine derivatives laurylpropylenediamine, $CH_3(CH_2)_{10}CH_2NH(CH_2)_3NH_2$, and N,N-bis(3-aminopropyl)laurylamine, $CH_3(CH_2)_{10}CH_2N((CH_2)_3NH_2$ and dimethylcoco fatty amine.

Particularly preferably, laurylpropylenediamine is used. By using this specific amine, cleaning performance and color stability of the concentrate can be improved compared with a concentrate having, for example, tetrakis(2-hydroxypropyl)-N,N,-N',N'-ethylenediamine. A similar improvement of cleaning performance is also achieved by using N,N-bis(3-aminopropyl)laurylamine, although then a greater amount, based on laurylpropylenediamine, must be used, which leads to a comparatively worse odor.

Preferably, the amount of the alkylamine (or of the two, three, four, etc. amines) is about 2 to about 10% by weight, more preferably about 3 to about 8% by weight, in particular about 4 to about 7% by weight, such as about 5 to about 6% by weight, for example, about 5.5% by weight.

The content of maleic and/or citric acid sets the desired pH in the concentrate and the dilute ready-to-use solution. It has surprisingly been found that other acids such as tartaric acid, lactic acid and benzoic acid are unsuitable, because although they set the pH in the dilute ready-to-use solution to the desired range, a sediment can form, however, in the concentrate.

Preferably, the amount of maleic acid and/or citric acid (preferably maleic acid) is about 0.1 to about 2.5% by weight, more preferably about 0.15 to about 1% by weight, such as about 0.2 to about 0.7% by weight, for example, about 0.28 to about 0.5% by weight.

The aromatic alcohol is preferably a phenoxyalkanol, a phenylmonolgycol ether of a oligoglycol having up to 20 ethylene oxide units, or a phenylalkanol, in which case the phenyl ring can in each case be substituted. Substituents which come into consideration, in this case, are in particular $C_1$- to $C_{18}$-alkyl groups. Preferably, the aromatic alcohol is 2-phenoxyethanol, phenoxy-2-propanol, 2-phenoxoy-1-propanol, 3-phenoxy-1-propanol, 1-phenoxy-2-butanol, 2-phenxoy-1-butanol, 1-phenylethyl alcohol, 2-phenylethyl alcohol, 3-phenyl-1-propanol or benzyl alcohol, or a mixture of two or more of these compounds.

The inventively used aromatic alcohols therefore also comprise mixtures of 1-phenoxy-2-propanol and 2-phenoxy-1-propanol. Phenoxypropanols display significantly better material compatibility than phenoxyethanol, but phenxoyethanol has a more pleasant odor. Those skilled in the art will make a suitable choice depending on the desired application, where the use of phenoxypropanols is preferred because of their good material compatibility.

Preferably, the amount of aromatic alcohol (or of the two, three, four, etc. aromatic alcohols) is about 15 to about 55% by weight, more preferably about 20 to about 50% by weight, in particular about 25 to about 45% by weight, for example, about 30 to about 40% by weight. In a particularly preferred embodiment, phenoxypropanols are used in an amount of about 35% by weight.

The inventive compositions can, furthermore, comprise one or more aliphatic alcohols, for example, ethanol, n-propanol or isopropanol, preferably in an amount up to about 20% by weight, more preferably about 5 to about 15% by weight, for instance, about 10% by weight, based on the concentrate, the use of ethanol being preferred. Furthermore, the inventive compositions can comprise additives such as corrosion inhibitors (for example, benzotriazole), complexing agents, perfumes and/or colorants in a customary amount.

The inventive concentrates are preferably formulated as aqueous concentrates and then comprise about 10 to about 40% by weight of water, more preferably about 15 to about 30% by weight, such as about 20 to about 25% by weight, for example, about 22.5% by weight of water. Preferably, inventive disinfectants are free from aldehyde, in particular free from formaldehyde, amine oxide, polymer and/or amino acid or amino acid derivative.

In a particularly preferred embodiment, the invention relates to a disinfectant in the form of a concentrate which comprises
   a) about 2 to about 3% by weight of benzalkonium chloride,
   b) about 10 to about 20% by weight of cocopropylenediamine guanidinium acetate,
   c) about 8 to about 12% by weight of $C_{13}$-isoalcohol-5EO,
   d) about 5 to about 6% by weight of laurylpropylenediamine,
   e) about 0.2 to about 0.7% by weight of maleic acid,
   f) about 30 to about 40% by weight of phenoxypropanols, and
   g) about 8 to about 10% by weight of ethanol, and also if appropriate additives such as corrosion inhibitors, perfumes and colorants in the customary amount.

Inventive compositions are preferably single-phase and clear, not only as concentrate, but also as dilute ready-to-use solution, this also applying to dilute ready-to-use solutions prepared using hard water. For use as ready-to-use solution diluted according to the invention, the inventive concentrates are used in an amount of about 0.2 to about 10% by weight in aqueous solution, preferably about 0.5 to about 8% by weight, such as about 0.8 to about 7% by weight, for example, about 1% by weight to about 5% by weight.

The invention relates furthermore to the use of $C_{10}$- to $C_{18}$-alcohol ethoxylates having 5 to 7 ethylene oxide units in a disinfectant which comprises quaternary ammonium salt, for improving the mycobactericidal activity of the disinfectant, compared with the activity of an essentially unchanged disinfectant composition, that is to say apart from the content of $C_{10}$- to $C_{18}$-alcohol ethoxylates having 5 to 7 ethylene oxide units, essentially identically formulated disinfectant which comprises alcohol ethoxylates having more than 7 ethylene oxide units. The said disinfectant in which the improvement in activity against mycobacteria is achieved by using $C_{10}$- to $C_{18}$-alcohol ethoxylate having 5 to 7 ethylene oxide units is preferably a disinfectant based on (i) quaternary ammonium salt and guanidine derivative, more preferably (ii) based on quaternary ammonium salt, guanidine derivative and alkylamine, in particular based on (iii) quaternary ammonium salt, guanidine derivative, alkylamine and organic acid, such as based on (iv) quaternary ammonium salt, guanidine derivatives alkylamine, organic acid (preferably maleic and/or citric acid) and aromatic alcohol.

The invention relates, furthermore, to the use of the concentrate or of the dilute (aqueous) ready-to-use solution as instrument disinfectant. Furthermore, the invention relates to the use of the concentrate or of the dilute (aqueous) ready-to-use solution for controlling mycobacteria, such as *Mycobacterium terrae* and *Mycobacterium tuberculosis*.

The inventive concentrates and dilute ready-to-use solutions (compositions) offer the following advantages:
   Using a relatively low amount of nonionic surfactant (alcohol ethoxylate) an improved activity against mycobacteria is achieved.
   The concentrates and ready-to-use solutions are storage-stable clear compositions, even in the event of dilution using hard water, turbidity and formation of sediment do not occur in the dilute ready-to-use solution.
   The compositions are excellent against mycobacteria such as *Mycobacterium terrae* and, furthermore, are bactericidally and fungicidally active.
   The compositions have an acceptable odor and are sufficiently material-compatible.
   The compositions, by selection of suitable amine, have a very good cleaning performance.

The advantages of the present invention are demonstrated, in particular, by the examples hereinafter. All percentages, unless stated otherwise, relate to the weight.

EXAMPLES

Formulations Used:

TABLE 1

| Constituents (1) | Comparison | Invention |
|---|---|---|
| Benzalkonium chloride | 2.5% | 2.5% |
| Cocopropylenediamine guanidinium acetate | 14% | 14% |
| Phenoxypropanol | 35% | 35% |
| Tetrakis-(2-hydroxypropyl)-N,N,N',N'-ethylenediamine | 5% | — |
| Laurylpropylenediamine | — | 5.5 |
| Maleic acid | — | approx. 0.5% |
| Tridecyl ethoxylate-12EO | 15% | — |
| Tridecyl ethoxylate-5EO | — | 10% |
| Ethanol | 10% | 10% |
| Water | to 100% | to 100% |
| pH | | |
| Concentrate | 8.5 | 9.3 |
| Dilute ready-to-use solution, 1–5% strength (2) | 8.5 | 8.5 |

(1) Data in percent by weight, further constituents: corrosion inhibitor, perfume, colorant;
(2) Amount of concentrate, based on the total amount of dilute ready-to-use solution.

Using the formulations of Table 1, a "quantitative microbe carrier test for evaluation of mycobactericidal activity of chemical disinfectants in the sector of human medicine, including instrument disinfectant (phase 2/step 2) EN 14563" was carried out. The test microbe used in these experiments was *Mycobacterium terrae*. The results are summarized in Table 2.

TABLE 2

| | Comparison | | | Invention | | |
|---|---|---|---|---|---|---|
| (1) | 15' | 30' | 60' | 15' | 30' | 60* |
| 1% | — | — | — | 2.28 | 2.71 | 5.79 |
| 2% | R | R | 0.34 | 3.53 | 5.85 | 6.57 |
| 3% | — | — | — | 5.05 | 5.95 | 6.87 |
| 4% | 1.29 | 1.33 | 2.85 | 5.81 | 6.85 | ≧7.17 |
| 5% | 1.60 | 3.19 | 5.47 | 5.93 | 6.55 | ≧7.17 |

(1) Amount of concentrate, based on the total amount of dilute ready-to-use solution.

The results verify that by using triisodecanol-5EO, the activity of the disinfectant can be outstandingly improved, although it was used in a lesser amount than in the comparative disinfectant using triisodecanol-12EO.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A composition which may be used as a concentrated alkaline disinfectant, said composition comprising:
    a) about 0.5% to about 10%, by weight, of a quaternary ammonium salt;
    b) about 1% to about 50%, by weight, of a guanidine derivative;
    c) about 1% to about 30%, by weight, of a $C_{10}$- to $C_{18}$-alcohol ethoxylate, wherein said ethoxylate has between about 5 and about 7 EO units;
    d) about 1% to about 15%, by weight, of alkylamine;
    e) about 0.05% to about 3%, by weight, of an acid, wherein said acid comprises at least one member selected from the group consisting of:
        1) maleic acid; and
        2) citric acid; and
    f) about 5% to about 60%, by weight, of aromatic alcohol.

2. The composition of claim 1, wherein said ammonium salt comprises benzalkonium chloride.

3. The composition of claim 1, wherein said guanidine derivative comprises cocopropylenediamine guanidinium acetate.

4. The composition of claim 1, wherein said alcohol ethoxylate comprises $C_{13}$-isoalcohol-5EO.

5. The composition of claim 1, wherein said amine comprises laurylpropylenediamine.

6. The composition of claim 1, wherein said acid comprises maleic acid.

7. The composition of claim 1, wherein said aromatic alcohol comprises a mixture of phenoxypropanols.

8. The composition of claim 1, further comprising about 1% to about 30%, by weight, of an aliphatic alcohol.

9. The composition of claim 8, wherein said aliphatic alcohol comprises ethanol.

10. The composition of claim 1, further comprising an additive, wherein said additive comprises at least one member selected from the group consisting of:
    a) corrosion inhibitors;
    b) complexing agents;
    c) perfumes; and
    d) colorants.

11. The composition of claim 1, comprising:
    a) about 2% to about 3%, by weight, of benzalkonium chloride;
    b) about 10% to about 20%, by weight, of cocopropylenediamine guanidinium acetate;
    c) about 8% to about 12%, by weight, of $C_{13}$-isoalcohol-5EO;
    d) about 5% to about 6%, by weight, of laurylpropylenediamine;
    e) about 0.2% to about -0.7%, by weight, of maleic acid;
    f) about 30% to about 40%, by weight, of phenoxypropanols; and further comprising
    g) about 8% to about 12%, by weight, of ethanol.

12. A composition which may be used as an aqueous ready-to-use solution for disinfecting, said composition comprising about 0.5% to about 10%, by weight, of a concentrate, wherein said concentrate comprises:
    a) about 0.5% to about 10%, by weight, of a quaternary ammonium salt;
    b) about 1% to about 50%, by weight, of a guanidine derivative;
    c) about 1% to about 30%, by weight, of a $C_{10}$- to $C_{18}$-alcohol ethoxylate, wherein said ethoxylate has between about 5 and about 7 EO units;
    d) about 1% to about 15%, by weight, of alkylamine;
    e) about 0.05% to about 3%, by weight, of an acid, wherein said acid comprises at least one member selected from the group consisting of:
        1) maleic acid; and
        2) citric acid; and
    f) about 5% to about 60%, by weight, of aromatic alcohol.

13. A method which may be used to disinfect an instrument, said method comprising treating an instrument with a composition, wherein said composition comprises:
    a) about 0.5% to about 10%, by weight, of a quaternary ammonium salt;
    b) about 1% to about 50%, by weight, of a guanidine derivative;
    c) about 1% to about 30%, by weight, of a $C_{10}$- to $C_{18}$-alcohol ethoxylate, wherein said ethoxylate has between about 5 and about 7 EO units;
    d) about 1% to about 15%, by weight, of alkylamine;
    e) about 0.05% to about 3%, by weight, of an acid, wherein said acid comprises at least one member selected from the group consisting of:
        1) maleic acid; and
        2) citric acid; and
    f) about 5% to about 60%, by weight, of aromatic alcohol.

14. A method which may be used to control mycobacteria, said method comprising controlling mycobacteria with a composition, wherein said composition comprises:
    a) about 0.5% to about 10%, by weight, of a quaternary ammonium salt;
    b) about 1% to about 50%, by weight, of a guanidine derivative;
    c) about 1% to about 30%, by weight, of a $C_{10}$- to $C_{18}$-alcohol ethoxylate, wherein said ethoxylate has between about 5 and about 7 EO units;
    d) about 1% to about 15%, by weight, of alkylamine;
    e) about 0.05% to about 3%, by weight, of an acid, wherein said acid comprises at least one member selected from the group consisting of:
        1) maleic acid; and
        2) citric acid; and
    f) about 5% to about 60%, by weight, of aromatic alcohol.

* * * * *